United States Patent
Kawa et al.

(10) Patent No.: US 7,572,435 B2
(45) Date of Patent: Aug. 11, 2009

(54) OIL BODIES FOR COSMETIC COMPOSITIONS CONTAINING CYCLOHEXYL CYCLOHEXANE

(75) Inventors: Rolf Kawa, Monheim (DE); Achim Ansmann, Erkrath (DE); Daniela Prinz, Dormagen (DE); Sabine Both, Duesseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 1027 days.

(21) Appl. No.: 10/507,674

(22) PCT Filed: Mar. 6, 2003

(86) PCT No.: PCT/EP03/02286

§ 371 (c)(1), (2), (4) Date: Apr. 8, 2005

(87) PCT Pub. No.: WO03/077879

PCT Pub. Date: Sep. 25, 2003

(65) Prior Publication Data

US 2005/0220826 A1  Oct. 6, 2005

(30) Foreign Application Priority Data

Mar. 15, 2002 (DE) ................... 102 11 618

(51) Int. Cl.
  *A61Q 5/00* (2006.01)
  *A61Q 17/04* (2006.01)
  *A61Q 19/00* (2006.01)
(52) U.S. Cl. ............... 424/70.1; 424/59; 424/401
(58) Field of Classification Search .......... None
  See application file for complete search history.

(56) References Cited

U.S. PATENT DOCUMENTS

| 4,778,619 | A | * | 10/1988 | Wakemoto et al. ....... 252/299.1 |
| 4,784,843 | A | | 11/1988 | Segnitz et al. |
| 5,356,627 | A | | 10/1994 | DaCunha |
| 5,705,169 | A | | 1/1998 | Stein et al. |
| 5,730,960 | A | | 3/1998 | Stein et al. |
| 5,879,667 | A | | 3/1999 | Hanna et al. |
| 5,945,091 | A | | 8/1999 | Habeck et al. |
| 6,193,960 | B1 | | 2/2001 | Metzger et al. |
| 6,217,792 | B1 | * | 4/2001 | Parri et al. ............. 252/299.61 |
| 6,342,469 | B1 | | 1/2002 | Lorant |

FOREIGN PATENT DOCUMENTS

| DE | 197 12 033 | 9/1998 |
| EP | 0 694 521 | 1/1996 |
| EP | 0 818 450 | 1/1998 |
| EP | 0693471 | 1/1998 |
| JP | 63 225316 | 9/1988 |
| JP | 8-41446 A | 2/1996 |
| JP | 8-506342 A | 7/1996 |
| JP | 11-5714 A | 1/1999 |
| JP | 2000-229814 A | 8/2000 |

OTHER PUBLICATIONS

Zeidler et al., "Über das Spreiten von Lipiden auf der Haut", Fette, Seifen, Anstrichmittel, vol. 87, 1985, pp. 403-408.
Lochhead et al., "Encyclopedia of Polymers and Thickeners for Cosmetics", Cosmetics & Toiletries, vol. 108, (May 1993), pp. 95-135.
P. Finkel, "Formulierung kosmetischer Sonnenschutzmittel", Parfumerie und Kosmetik, 80, No. 3, 1999, pp. 10-12, 14-16.

* cited by examiner

*Primary Examiner*—Jyothsna A Venkat

(57) ABSTRACT

A cosmetic composition containing: (a) an aqueous phase; (b) an oil phase containing cyclohexyl cyclohexane; (c) optionally, a surfactant; and (d) optionally, an auxiliary oil component.

12 Claims, No Drawings

OIL BODIES FOR COSMETIC COMPOSITIONS CONTAINING CYCLOHEXYL CYCLOHEXANE

BACKGROUND OF THE INVENTION

This application is a 371 of PCT/EP03/02286 filed Mar. 6. 2003, claiming priority from DE 102 11 618.0 filed Mar. 15, 2002, the entire contents of each application are incorporated herein by reference.

This invention relates to new hydrocarbon-based oil components which may readily be incorporated in cosmetic and pharmaceutical preparations, show good dermatological compatibility and provide cosmetic formulations with a particularly light feeling on the skin.

Consumers expect cosmetic skin- and hair-care emulsions to satisfy a range of requirements. Apart from the cleaning and skin/hair-care effects which determine the intended application, value is placed on such diverse parameters as very high dermatological compatibility, elegant appearance, optimal sensory impression and stability in storage.

Besides a number of surfactants, preparations used to clean and care for the human skin and hair contain, above all, oil components and water. The oil components/emollients used include, for example, hydrocarbons, ester oils and vegetable and animal oils/fats/waxes. In order to meet stringent commercial requirements in regard to sensory properties and optimal dermatological compatibility, new oil components and emulsifier mixtures are continually being developed and tested. A large number of natural and synthetic oils, for example almond or avocado oil, ester oils, ethers, alkyl carbonates, hydrocarbons and silicone oils, are used in the production of cosmetic or pharmaceutical preparations. A key function of the oil components—besides their care effect which is directly related to lipid layer enhancement of the skin—is to provide the skin of consumers with a non-sticky, almost instantaneous and long-lasting feeling of smoothness and suppleness.

The subjective feeling on the skin can be correlated and objectivized with the physicochemical parameters of the spreading of the oil components on the skin, as illustrated by U. Zeidler in Fette, Seifen, Anstrichmitt. 87, 403 (1985). According to this reference, cosmetic oil components can be classified as low-spreading (below 300 $mm^2/10$ mins.), medium-spreading (around 300 to 1000 $mm^2/10$ mins.) and high-spreading oils (above 1000 $mm^2/10$ mins.). If a high-spreading oil is used as the oil component in a predetermined formulation, the required feeling of smoothness of the skin is achieved very quickly and, where cyclomethicones, for example Dow Corning 245 fluid (Dow Corning Corporation) or Abil B 8839 (Goldschmidt Chemical Corporation), are used, a velvety feeling desirable to the consumer is also obtained. Unfortunately, the experience does not last long because the high volatility of the last-mentioned structures means that the pronounced feeling of smoothness and hence the velvety feel disappear very quickly, leaving the skin with an unpleasant, dull feeling.

The problem addressed by the present invention was to provide improved, high-spreading oil components which would impart an almost instantaneous and relatively long-lasting feeling of smoothness to the skin and which would show good dermatological compatibility. In addition, the new structures would lend themselves to simple and stable incorporation in emulsions and would be hydrolysis-stable in the event of pH variations.

BRIEF SUMMARY OF THE INVENTION

Accordingly, the present invention relates to a cosmetic preparation containing at least one aqueous phase and an oil phase insoluble in the aqueous phase, the oil phase completely or partly containing cyclohexyl cyclohexane. Cyclohexyl cyclohexane is a compound known per se which can be obtained, for example, by base-catalyzed aldol condensation of two parts cyclohexanone and subsequent hydrogenation. Cyclohexyl cyclohexane itself is a colorless liquid which can be produced in highly pure form ($\geqq$99%). It is high-spreading under Zeidler's above definition (spreading values of at least 1,600 $mm^2/10$ mins.).

Cosmetic Preparations

The compound according to the invention allows the production of stable cosmetic emulsions. These cosmetic emulsions are preferably body care formulations, for example in the form of creams, milks, lotions, sprayable emulsions, products for eliminating body odor, etc. The compound according to the invention may also be used in surfactant-containing formulations such as, for example, foam and shower baths, hair shampoos and care rinses. These formulations preferably contain the cyclohexyl cyclohexane in total quantities of 0.1 to 40% by weight and preferably in total quantities of 0.1 to 30% by weight. The cosmetic preparations contain water and the oil phase alongside one another in the form of emulsions or dispersions, preferably w/o or o/w emulsions. Depending on the particular application envisaged, the cosmetic formulations contain a number of other auxiliaries and additives, such as, for example, surfactants, other oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, etc. which are listed by way of example in the following.

DETAILED DESCRIPTION OF THE INVENTION

Surfactants

The surfactants present may be anionic, nonionic, cationic and/or amphoteric or zwitterionic surfactants. In surfactant-containing cosmetic preparations such as, for example, shower gels, foam baths, shampoos, etc., at least one anionic surfactant is preferably present. In this case, the percentage content of surfactants is normally about 1 to 30% by weight, preferably 5 to 25% by weight and more particularly 10 to 20% by weight.

Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride(ether)sulfates, fatty acid amide(ether)sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl(ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works in this field. Typical examples of particularly suitable mild, i.e. particularly dermatologically compatible, surfactants are fatty alcohol polyglycol ether sulfates, monoglyceride sulfates, mono-and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Body care preparations, such as creams, lotions and milks, normally contain a number of other oil components and emollients which contribute towards further optimizing their sensory properties. The oil components are normally present in a total quantity of 0.1 to 50% by weight, preferably 5 to 25% by weight and more particularly 5 to 15% by weight. Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl paelmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, such as Dicaprylyl Carbonate (Cetiol® CC) for example, Guerbet carbonates based on $C_{6-18}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, such as Dicaprylyl Ether (Cetiol® OE) for example, ring opening products of epoxidized fatty acid esters with polyols, silicone oils (cyclomethicone, silicon methicone types, etc.) and/or aliphatic or naphthenic hydrocarbons such as, for example, squalane, squalene or dialkyl cyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide onto linear $C_{8-22}$ fatty alcohols, onto $C_{12-22}$ fatty acids, onto alkyl phenols containing 8 to 15 carbon atoms in the alkyl group and onto alkylamines containing 8 to 22 carbon atoms in the alkyl group;

alkyl oligoglycosides containing 8 to 22 carbon atoms in the alkyl group and ethoxylated analogs thereof;

addition products of 1 to 15 mol ethylene oxide onto castor oil and/or hydrogenated castor oil;

addition products of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide;

partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide;

mixed esters of pentaerythritol, fatty acids, citric acid and fatty alcohol and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethyleneglycol-30 Dipolyhydroxystearate;

polymer emulsifiers, for example Pemulen types (TR-1, TR-2) of Goodrich;

polyalkylene glycols and glycerol carbonate.

Ethylene Oxide Addition Products

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers

Typical anionic emulsifiers are aliphatic fatty acids containing 12 to 22 carbon atoms such as, for example, palmitic acid, stearic acid or behenic acid and dicarboxylic acids containing 12 to 22 carbon atoms such as, for example, azelaic acid or sebacic acid.

Amphoteric and Cationic Emulsifiers

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

According to the invention, preferred cosmetic and/or pharmaceutical preparations contain (a) 0.1 to 30% by weight cyclohexyl cyclohexane, (b) 0.1 to 20% by weight of surfactants and/or emulsifiers and/or co-emulsifiers, (c) 0.1 to 40% by weight oil components and (d) 0.1 to 98% by weight of water, based on the composition as a whole.

Fats and Waxes

Fats and waxes are added to the body care products both as care components and to increase the consistency of the cosmetic preparations. Typical examples of fats are glycerides, i.e. solid or liquid, vegetable or animal products which consist essentially of mixed glycerol esters of higher fatty acids. Fatty acid partial glycerides, i.e. technical mono- and/or diesters of glycerol with $C_{12-18}$ fatty acids, such as for example glycerol mono/dilaurate, palmitate or stearate, may also be used for this purpose. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerol-phosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The other consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequato® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacryl-amide/methyl methacrylate/tert.-butylaminoethyl methacrylate/2-hydroxy-propyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone, as described in EP 0818450 A1, or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789) or 1-phenyl-3-(4'-isopropylphenyl)-propane-1,3-dione and the enamine compounds described in DE 19712033 A1 (BASF). The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to μmol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nor-dihydroguaiac resin acid, nordihydroguaiaretic acid, trihydroxybutyrophenone, uric acid and derivatives thereof, mannose and derivatives thereof, superoxide dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-noctyl amide or salicylic acid-n-decyl amide.

Enzyme Inhibitors

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor Absorbers

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, ptert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, lemon balm oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components,
nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers or swelling agents can be found in R. Lochhead's review in Cosm. Toil. 108, 95 (1993).

Insect Repellents

Suitable insect repellents are N,N-diethyl-m-toluamide, pentane-1,2-diol or 3-(N-n-butyl-N-acetylamino)-propionic acid ethyl ester), which is marketed under the name of Insect Repellent® 3535 by Merck KGaA, and butyl acetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Perfume Oils and Aromas

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

Dyes

Suitable dyes are any of the substances suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

EXAMPLES

Preparation of Cyclohexyl Cyclohexane:

140 g KOH (solid) are added to 2,000 g (20.41 mol) cyclohexanone. The mixture is heated under reflux with stirring. After 0.5 h, the reaction is terminated. The mixture is analyzed by GC analysis.

The reaction mixture has the following composition:
1. cyclohexanone: 35.6%
2. dimer of α/β-unsaturated ketone: 56.9%
3. trimer of α/β-unsaturated ketone: 4.5%
4. rest: 3%

After cooling, most of the KOH remains in the flask. The mixture is washed until neutral with acidified dist. water (pH 3) and separated by distillation from unreacted cyclohexanone, water and high-boiling components. 720 g of a cyclohexanone/water mixture as the initial fraction distillate, 1100 g dimer product and 170 g bottom product (discarded) are obtained.

Hydrogenation:

Apparatus: Hydrogenation Autoclave with Hydrogen Inlet, Heating System Procedure:

4.4% by weight nickel-containing hydrogenation catalyst is added to 1,000 g unsaturated α/β-dimer ketone. The mixture is heated to 245° C. and hydrogen is added. A hydrogen pressure of 20 bar is applied for 4 hours to replace the hydrogen reacted off. After termination of the reaction, the mixture is cooled to room temperature. The mixture obtained is purified by fractional distillation. 5 g initial fraction distillate and 980 g main fraction distillate are obtained at 148° C. bottom temperature/1 mbar head pressure. The bottom product is discarded. According to GC-MS analysis, the main fraction consists of 99% cyclohexyl cyclohexanone.

Performance Tests:

The following Examples describe the performance of the oil components according to the invention by comparison with commercially available high-spreading oils.

Standard Emulsion—Quantities in % by Weight, Based on The Final Concentration

| | |
|---|---|
| Cyclohexyl cyclohexane | 20 |
| Eumulgin B2 Ceteareth-2 | 2 |
| Lanette O Cetearyl Alcohol | 2 |
| Glycerol | 5 |
| Carbopol 981 (Carbomer) | 0.2 |
| NaOH pH 7 | pH 7 |
| Water, preservative | to 100 |

Subjective Evaluation of Skin Smoothness

A panel of 5 experienced people tested formulations based on a standard emulsion containing various high-spreading oil components for their subjective skin feeling. Evaluation was based on a scale of 1 (hardly any smoothing, rapid reduction in the feeling of smoothness, poor velvety feel) to 6 (rapid, uniform smoothness, long-lasting feeling of smoothness, good velvety feel). The figures in the Table are mean values. Example 1 corresponds to the invention, Examples C1 to C4 are intended for comparison.

| Example | Intensity of skin smoothness | Intensity of velvety feel | Duration of experience |
|---|---|---|---|
| 1 | 6 | 6 | 6 |
| C1 | 5 | 4 | 2 |
| C2 | 4 | 4 | 2 |
| C3 | 3 | 1 | 1 |
| C4 | 3 | 1 | 1 |

1 - oil component according to the invention (spreading value: 1600 mm$^2$/10 mins.)
C1 - Dow Corning 245 fluid (spreading value: >1600 mm$^2$/10 mins.)
C2 - Abil B 8839 (spreading value: >1600 mm$^2$/10 mins.)
C3 - Crodamol IPM (Isopropyl Myristate) (spreading value: 1000 mm$^2$/10 mins.)
C4 - Cetiol A (Hexyl Laurate) (spreading value: 1100 mm$^2$/10 mins)

In another test, the emulsifying behavior of the standard emulsion was evaluated as a function of the oils used. As evaluation criteria, the size of the droplets was evaluated by microscope and the appearance of the test emulsion was visually compared with a standard, as described in Parfümerie und Kosmetik, Vol. 80, No. 3/99, page 22. The evaluation was based on a scale ranging from droplet size A: very fine to droplet size E: very coarse. At the same time, phase stability was evaluated after storage for 3 months at 40° C. Evaluation was based on a scale ranging from 1: stable to 6: separation into two phases.

| Example | Droplet size | Phase stability |
|---|---|---|
| 1 | A | 1 |
| C1 | D | 5 |
| C2 | E | 6 |
| C3 | C | 3 |
| C4 | C | 2 |

The following Tables show examples of formulations which demonstrate the manifold potential applications of the oil phases according to the invention.

TABLE 1

O/W sun protection emulsions
Quantities are in % by weight of the commercially available substances in the composition as a whole

| Component | 1 | 2 | 3 | 4 | 5 | 6 | 7 | 8 | 9 | 10 | 11 |
|---|---|---|---|---|---|---|---|---|---|---|---|
| L = Lotion, C = Cream | L | C | S | L | C | L | L | C | L | C | L |
| Eumulgin ® VL 75 | | | | | | 4 | 4 | 2 | | | |
| Eumulgin ® B2 | 2 | | | | | | | | | | |
| Tween ® 60 | | | | 1 | | | | | | | |
| Myrj ® 51 | | 3 | | 2 | | | | | | | |
| Cutina ® E 24 | 1 | | | 1 | | | | | | | |
| Hostaphat ® KL 340 N | | | | | | | | | | | 2 |

TABLE 1-continued

O/W sun protection emulsions
Quantities are in % by weight of the commercially available substances in the composition as a whole

| Component | 1 | 2 | 3 | 4 | 5 | 6 | 7 | 8 | 9 | 10 | 11 |
|---|---|---|---|---|---|---|---|---|---|---|---|
| Lanette ® E | | | 0.5 | | | | | 0.5 | | | |
| Amphisol ® K | | | 1 | | | 1 | | 0.5 | | 1 | |
| Sodium stearate | | | | | | | 1 | | | | 2 |
| Emulgade ® PL 68/50 | | | 1 | | 5 | | | | | 4 | |
| Tego ® Care 450 | | | | | | | | | | 3 | |
| Cutina ® MD | 2 | | | 6 | | | 4 | | | 6 | |
| Lanette ® 14 | 1 | | | 1 | | | | 2 | | | 4 |
| Lanette ® O | 1 | 6 | | | 5 | 2 | | 2 | | | |
| Antaron V 216 | | | 1 | | 2 | 2 | | | | 1 | |
| Emery ® 1780 | | | | | 0.5 | 0.5 | | | | | |
| Lanolin, anhydrous, USP | | | | | | | 5 | | | | |
| Cyclohexyl cyclohexane | 2 | 2 | 4 | 1 | 2 | 2 | 2 | 1 | 2 | 2 | 1 |
| Myritol ® PC | | | | | 5 | | | | | | |
| Myritol ® 331 | 5 | | 8 | | | 6 | | 10 | | 2 | |
| Finsolv ® TN | | | 1 | | | | | 1 | 8 | | |
| Cetiol ® CC | | 2 | 5 | | | 4 | 4 | 2 | | 2 | |
| Cetiol ® OE | | | 3 | | | | | | 2 | 3 | |
| Dow Corning DC ® 244 | 4 | | 1 | | 5 | | | 2 | | | 2 |
| Dow Corning DC ® 2502 | | 1 | | | 2 | | | | | | |
| Squatol ® S | | | | | | | 4 | | | | |
| Silikonöl Wacker AK ® 350 | | 2 | | | | | | | | | |
| Cetiol ® 868 | | | | | 2 | | 4 | | | | 7 |
| Cetiol ® J 600 | | | | | 3 | 2 | | | | 5 | |
| Mineral oil | | | | 9 | | | | | | | |
| Cetiol ® B | | | 1 | | | | | | | 2 | |
| Eutanol ® G | | | | | | | | | | | |
| Eutanol ® G 16 | | | | | | | | | | | |
| Cetiol ® PGL | | 5 | | | | | | | | 5 | |
| Almond oil | | 2 | | | | | 1 | | | | |
| Photonyl ® LS | | | | 2 | | | | | | 2 | |
| Panthenol | | | | | | 1 | | | | | |
| Bisabolol | | | | | | 0.2 | | | | | |
| Tocopherol/Tocopherylacetate | | | | | | 1 | | | | | |
| Photonyl ® LS | | | | | | | | | | | |
| Neo Heliopan ® Hydro (Na salt) | 2 | | 2.2 | 3 | 3 | | | | | 2 | |
| Neo Heliopan AP (Na salt) | 2 | | | 1.5 | 2 | 2 | | 1 | | | 1 |
| Neo Heliopan ® 303 | 3 | 5 | 9 | 4 | | | | | | | |
| Neo Heliopan ® BB | | | | 1 | | | | | | | 2 |
| Neo Heliopan ® MBC | 2 | | 3 | | 2 | 2 | 2 | | | | 1 |
| Neo Heliopan ® OS | | | | | | | | | 10 | 7 | |
| Neo Heliopan ® E 1000 | | 7.5 | | 6 | | | | | | | 6 |
| Neo Heliopan ® AV | | | 7.5 | | 7.5 | 4 | 5 | | | | |
| Uvinul ® T 150 | 2 | | | 2.5 | | | 1 | | | | |
| Parsol ® 1789 | | 1 | 1 | | | 2 | | 2 | | 2 | |
| Zinc oxide NDM | 10 | | 5 | | 10 | | 3 | | | 5 | 4 |
| Eusolex ® T 2000 | | | | 5 | | 3 | 3 | | | | 4 |
| Veegum ® Ultra | | | 0.75 | | | | | 1 | 1 | | |
| Keltrol ® T | | | 0.25 | | | | | 0.5 | 0.5 | | |
| Carbopol ® 980 | | 0.5 | | 0.2 | 0.2 | 0.2 | | 0.5 | 0.1 | 0.3 | 0.2 |
| Ethanol | | | | | | | | | 10 | | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservative, NaOH | | | | | | q.s. | | | | | |
| Water | | | | | | to 100 | | | | | |

TABLE 2

O/W sun protection emulsions
Quantities are in % by weight of the commercially available substances in the composition as a whole

| Component | 12 | 13 | 14 | 15 | 16 | 17 | 18 | 19 | 20 | 21 | 22 |
|---|---|---|---|---|---|---|---|---|---|---|---|
| L = Lotion, C = Cream | L | L | L | C | L | C | S | C | C | L | L |
| Eumulgin ® VL 75 | 4 | 3 | 4.5 | | 3 | | | | 4 | | |
| Eumulgin ® B2 | | | | | | | | | | 1 | |
| Tween ® 60 | | | | | | | | | | 1 | |
| Myrj ® 51 | | | | | | | | | | | |
| Cutina ® E 24 | | | | | 2 | | | | | | |
| Hostaphat ® KL 340 N | | | | | | | | | | | 0.5 |

TABLE 2-continued

O/W sun protection emulsions
Quantities are in % by weight of the commercially available substances in the composition as a whole

| Component | | | | | | | | | | | |
|---|---|---|---|---|---|---|---|---|---|---|---|
| Lanette ® E | 0.5 | | 0.5 | 0.5 | | 0.1 | | 0.5 | | | |
| Amphisol ® K | 0.5 | | | | 1 | 1 | 1 | | | | |
| Sodium stearate | | | | | 1 | | | | | | |
| Emulgade ® PL 68/50 | | 6 | | | | 4.5 | 1 | 5 | | | |
| Tego ® Care 450 | 1 | | | | | | | | 4 | | |
| Cutina ® MD | 1 | | | 8 | 6 | 1 | | | | 4 | 1 |
| Lanette ® 14 | | 2 | | | | | | 2 | | 1 | |
| Lanette ® O | | | 2 | | | | | | 1 | 1 | |
| Antaron V 220 | 1 | | | 2 | | | 0.5 | | | 2 | 0.5 |
| Cyclohexyl cyclohexane | 4 | 2 | 4 | 6 | 10 | 4 | 2 | 8 | 2 | 1 | 3 |
| Myritol ® PC | | | | | | | | | 5 | | |
| Myritol ® 331 | 12 | | 12 | | | 8 | 8 | | | 10 | 8 |
| Finsolv ® TN | | | | | 5 | | | 3 | 3 | | |
| Cetiol ® CC | 6 | | 6 | | | 5 | 5 | | | | |
| Cetiol ® OE | | | | 2 | | | | | | | 2 |
| Dow Corning DC ® 244 | | 2 | | 1 | | | | | | | |
| Dow Corning DC ® 2502 | | 1 | | 1 | | | | | | | |
| Ceraphyl ® 45 | | | | | | | | | | 2 | 2 |
| Silikonöl Wacker AK ® 350 | | | | 1 | | | | | | | |
| Cetiol ® 868 | | 2 | | | | | | | | | |
| Cetiol ® J 600 | | 2 | | | | | | | | | |
| Mineral oil | | | | 10 | | | | | | | |
| Cetiol ® B | 4 | | 4 | | | | | 4 | | | |
| Eutanol ® G | | 3 | | | | 3 | | | | | |
| Eutanol ® G 16 S | 10 | | | | | | | | | | |
| Cetiol ® PGL | | | | | | | | | 2 | | |

| Component | 22 | 23 | 24 | 25 | 26 | 27 | 28 | 29 | 30 | 31 | 32 |
|---|---|---|---|---|---|---|---|---|---|---|---|
| Photonyl ® LS | | | | | | | | | | 2 | |
| Panthenol | | | | | | 1 | | | | | |
| Bisabolol | | | | | | 0.2 | | | | | |
| Tocopherol/ Tocopherylacetate | | | | | | 1 | | | | | |
| Neo Heliopan ® Hydro (Na salt) | | | | | | | | | | 3 | |
| Neo Heliopan AP (Na salt) | | 2 | | 2 | | | 2 | | | | 1 |
| Eusolex ® OCR | 6 | | 9 | | 5 | 7 | 9 | | 4 | | 7 |
| Neo Heliopan ® BB | | | | | | | | | 1 | 1 | 1 |
| Neo Heliopan ® MBC | | 2 | | 1 | | | | | 3 | 1 | 3 |
| Neo Heliopan ® OS | 2 | | | | | | | | 7 | | |
| Neo Heliopan ® E1000 | | 4 | | | | | | 5 | | | |
| Neo Heliopan ® AV | | 4 | 7.5 | 5 | | | | 5 | 4 | 7.5 | |
| Uvinul ® T 150 | 1 | | | | | | | | 1.3 | 1 | 1 |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | | 10 | | 2 | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Pemulen ® TR 2 | | 0.3 | | 0.3 | | | 0.1 | 0.2 | | | 0.3 |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |
| Water/preservative/NaOH | | | | | to 100/q.s./q.s | | | | | | |

TABLE 3

W/O sun protection emulsions
Quantities are in % by weight of the commercially available substances in the composition as a whole

| Component | 33 | 34 | 35 | 36 | 37 | 38 | 39 | 40 | 41 | 42 | 43 |
|---|---|---|---|---|---|---|---|---|---|---|---|
| L = Lotion; C = Cream | C | L | C | L | C | L | L | L | L | C | C |
| Dehymuls ® PGPH | 4 | 2 | 1 | 3 | 3 | 1 | 1 | 2 | 2 | 4 | 1 |
| Monomuls ® 90-O18 | | | 2 | | | | | | | | |
| Lameform ® TGI | 2 | | 4 | | 3 | | | | | 1 | 3 |
| Abil ® EM 90 | | | | | | | 4 | | | | |
| Glucate ® DO | | | | | | | | | | | 3 |
| Isolan ® PDI | | | | | | 4 | | 2 | | | |
| Arlacel ® 83 | | | | 2 | | | | | | | |
| Elfacos ® ST9 | | | | | | | | | | 2 | |
| Elfacos ® ST37 | | | | | | | | | | | |

TABLE 3-continued

W/O sun protection emulsions
Quantities are in % by weight of the commercially available substances in the composition as a whole

| Component | 33 | 34 | 35 | 36 | 37 | 38 | 39 | 40 | 41 | 42 | 43 |
|---|---|---|---|---|---|---|---|---|---|---|---|
| Arlacel ® P 135 | | 2 | | | | | | | | | |
| Dehymuls ® HRE 7 | | | | | | | | | | | |
| Zinc stearate | 1 | | | 1 | 1 | | | 1 | | 1 | |
| Microcrystalline wax | | | 5 | | | 2 | | | | | 5 |
| Beeswax | 1 | | | 1 | | | | 5 | | 7 | |
| Tego ® Care CG | | | | | 1 | | | | | | .5 |
| Prisorine ® 3505 | 1 | | 1 | 1 | | 1 | 1 | | | | 1 |
| Emery ® 1780 | | | 5 | | | | | | | 4 | |
| Wool wax alcohol, anhydrous, USP | | | | | | | | | | | 1 |
| Antaron V 216 | 2 | | | | | | | | | | |
| Cyclohexyl cyclohexane | 3 | 4 | 2 | 1 | 10 | 2 | 2 | 6 | 3 | 12 | 1 |
| Myritol ® PC | | | | | 3 | | | 4 | | | |
| Myritol ® 331 | 10 | | | | 3 | 6 | | | | | 8 |
| Finsolv ® TN | | | | 5 | | | 5 | | | | |
| Cetiol ® CC | 12 | 22 | | | | 2 | | | 2 | | 5 |
| Cetiol ® OE | | | | | 4 | | 5 | | 4 | 2 | |
| Dow Corning DC ® 244 | | | | | | 2 | | | | | |
| Dow Corning DC ® 2502 | | | 1 | | 2 | | | | | | |
| Prisorine ® 3758 | | | | | | | | | | 2 | |
| Silikonöl Wacker AK ® 350 | | | | 4 | | | | 3 | | | |
| Cetiol ® 868 | | | | | | | | | | 2 | |
| Eutanol ® G 16 | | 3 | | | | | | | | | |
| Eutanol ® G 16S | | | | | | | | | | | |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | | 2 | 4 | | | | | 3 | |
| Eutanol ® G | | | | 3 | | | | 8 | | | |
| Cetiol ® PGL | | 11 | | | | 4 | | | 9 | | |
| Almond oil | | | | | 1 | | 5 | | | | |
| Photonyl ® LS | | 2 | | 1 | | | | | 4 | | |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate x 7 water | 1 | | | | | | | | | | |
| Neo Heliopan ® Hydro (Na salt) | | 2 | | 3 | | | | 2 | | | |
| Neo Heliopan AP (Na salt) | 2 | 1 | | | 2 | | | 1 | 2 | | 1 |
| Neo Heliopan ® 303 | | | | | 4 | | | | | 6 | |
| Neo Heliopan ® BB | | 4 | 2 | | | | 2 | | | | |
| Neo Heliopan ® MBC | | | | | | | | 4 | | 3 | |
| Neo Heliopan ® OS | | | | | | | | | | | |
| Neo Heliopan ® E 1000 | | | | | | | | | 5 | | |
| Neo Heliopan ® AV | | 3 | 6 | 6 | | 7.5 | 7.5 | | 5 | | 7.5 |
| Uvinul ® T 150 | | | | | 2.5 | | | 1 | | 2 | |
| Parsol ® 1789 | | 2 | | | | | | 1 | | 2 | |
| Zinc oxide NDM | | | | | | 6 | | | | | |
| Eusolex ® T 2000 | 15 | | 10 | | 5 | 4 | | | | | 4 |
| Ethanol | | | | | | | | | | 8 | |
| Butylene glycol | | | 2 | 6 | | | 2 | 5 | | | 2 |
| Glycerin | 5 | 3 | 3 | | 5 | 3 | 2 | | 10 | 4 | |
| Water, preservative | | | | | to 100, q.s. | | | | | | |

TABLE 4

W/O sun protection emulsions
Quantities are in % by weight of the commercially available substances in the composition as a whole

| Component | 44 | 45 | 46 | 47 | 48 | 49 | 50 | 51 | 52 | 53 | 54 |
|---|---|---|---|---|---|---|---|---|---|---|---|
| L = Lotion; C = Cream | L | C | L | L | C | L | L | L | L | C | C |
| Dehymuls ® PGPH | 3 | 1 | 5 | 1 | 1 | 3 | 2 | 4 | 0.5 | 1 | 4 |
| Monomuls ® 90-O18 | | | 1 | | | | | | | | |
| Lameform ® TGI | | | | | 4 | | | 1 | | 3 | 1 |
| Abil ® EM 90 | | | | 1 | | | | | | 2 | |
| Glucate ® DO | | | | 3 | | | | | 2 | | |
| Isolan ® PDI | | 3 | | | | 4 | | | | | |
| Arlacel ® 83 | | | | | | 3 | | | | | |
| Elfacos ® ST9 | | | | | | | | | | | 2 |
| Elfacos ® ST37 | 2 | | | | | | | | | | |

TABLE 4-continued

W/O sun protection emulsions
Quantities are in % by weight of the commercially available substances in the composition as a whole

| Component | 44 | 45 | 46 | 47 | 48 | 49 | 50 | 51 | 52 | 53 | 54 |
|---|---|---|---|---|---|---|---|---|---|---|---|
| Arlacel ® P 135 | | | | | | 3 | | | | | |
| Dehymuls ® HRE 7 | | | | | | | | | 4 | | |
| Zinc stearate | | | 2 | 2 | 1 | 1 | | | 1 1 | | |
| Microcrystalline wax | | | | | 4 | | 1 | | | 4 | |
| Beeswax | | | 4 | | 2 | | | 1 | | 2 | 1 |
| Tego ® Care CG | | | | | | | | | | | |
| Isostearic acid | 1 | 1 | | | | | 1 | 1 | | 1 | 1 |
| Emery ® 1780 | | | 7 | 3 | | | | | | | |
| Wool wax alcohol, anhydrous, USP | | | | | | | | | | | |
| Antaron V 220 | | 0.5 | 2 | 1 | 1 | 1 | | | | | |
| Cyclohexyl cyclohexane | 2 | 4 | 3 | 3 | 2 | 2 | 1 | | 3 3 | 1 | 4 |
| Myritol ® PC | | | | | | | | | | | |
| Myritol ® 331 | 4 | 2 | 3 | | 5 | | | 8 | 5 | 4 | |
| Finsolv ® TN | | 5 | 5 | | | 7 | | | | | |
| Cetiol ® CC | 3 | 1 | | | | | 3 | 16 | | | 12 |
| Cetiol ® OE | | 3 | | 2 | | | 3 | | | | |
| Dow Corning DC ® 244 | | 4 | | 2 | | | | | | | |
| Dow Corning DC ® 2502 | | | | 1 | | | | | | | |
| Prisorine ® 3578 | | 1 | | | | | | | | | |
| Silikonöl Wacker AK ® 350 | | | | 1 | | | | | | | |
| Cetiol ® 868 | | | | | | | | | | | |
| Eutanol ® G 16 | | | | | | | | | | | 3 |
| Eutanol ® G 16S | | | | | | | | | | | 7 |
| Cetiol ® J 600 | | | | 3 | | | | | | | |
| Ceraphyl ® 45 | | | | 1 | | | | | 5 | 4 | |
| Mineral oil | | | | | | | 9 | | | | |
| Cetiol ® B | | | | | 3 | 3 | | 2 | 2 | | |
| Eutanol ® G | | | | 2 | | | | | 5 | | |
| Cetiol ® PGL | | | | | | | | | 2 | | |
| Almond oil | | | 2 | | | | | | | | |
| Photonyl ® LS | | | | | | | 3 | | | | 2 |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate × 7 water | | | | | | 1 | | | | | |
| Neo Heliopan ® Hydro (Na salt) | | 4 | | | | | | 4 | | | |
| Neo Heliopan AP (Na salt) | 2 | | | 1 | 2 | | 1 | | | | |
| Neo Heliopan ® 303 | 6 | 2 | | | | | | | 6 | | |
| Neo Heliopan ® BB | | 2 | | 2 | | 2 | | | | | |
| Neo Heliopan ® MBC | 2 | | | | 3 | | 4 | | 2 | | |
| Neo Heliopan ® OS | | | | | 10 | | 8 | | | | |
| Neo Heliopan ® E 1000 | | | 5 | 6 | | | | | | 5 | |
| Neo Heliopan ® AV | | 5 | 5 | | | 7.5 | | | | 5 | |
| Uvinul ® T 150 | 1 | | | | 2 | 2 | | | 3 | 2 | |
| Parsol ® 1789 | | 1 | 1 | | | | 1 | | 0.5 | | |
| Z-Cote ® HP 1 | 4 | 10 | | | | | | 5 | | | 5 |
| Titanium dioxide T 805 | | | | | 2 | | 3 | | 7 | 4 | 7 |
| Ethanol | | | | | 8 | 10 | | | | | |
| Butylene glycol | 5 | 1 | | | 3 | 3 | | | 8 | 2 | |
| Glycerin | | | 6 | 2 | | | 5 | 5 | | 3 | 5 |
| Water, preservative | | | | | to 100, q.s. | | | | | | |

TABLE 5

W/O care emulsions
Quantities are in % by weight of the commercially available substances in the composition as a whole

| Component | 55 | 56 | 57 | 58 | 59 | 60 | 61 | 62 | 63 | 64 | 65 |
|---|---|---|---|---|---|---|---|---|---|---|---|
| L = Lotion, C = Cream | C | L | C | L | C | L | L | L | C | C | C |
| Dehymuls ® PGPH | 1 | 3 | 1 | 2 | 3 | 1 | 1 | 2 | 1 | 1 | 1 |
| Monomuls ® 90-O18 | 2 | | | | | | | | 2 | | 2 |
| Lameform ® TGI | 4 | 1 | | | 3 | | | 1 | 4 | 3 | 3 |
| Abil ® EM 90 | | | | | | 4 | | | | | |
| Isolan ® PDI | | | | | | | 4 | | | | |
| Glucate ® DO | | | | 5 | | | | | | | |
| Arlacel ® 83 | | | 5 | | | | | | | | |
| Dehymuls ® FCE | | | | | | | | | | | |
| Dehymuls ® HRE 7 | | | | | | | | | 4 | | 1 |

TABLE 5-continued

W/O care emulsions
Quantities are in % by weight of the commercially available substances in the composition as a whole

| Component | 55 | 56 | 57 | 58 | 59 | 60 | 61 | 62 | 63 | 64 | 65 |
|---|---|---|---|---|---|---|---|---|---|---|---|
| Zinc stearate | 2 | 1 |  | 1 | 1 |  |  | 1 | 1 | 1 |  |
| Microcrystalline wax |  |  | 5 |  |  | 2 |  |  |  |  | 5 |
| Beeswax | 4 |  |  | 1 |  |  |  | 1 | 4 | 7 |  |
| Tego Care ® CG |  |  |  |  | 1 |  |  |  |  |  | 0.5 |
| Prisorine ® 3505 |  |  | 1 | 1 |  | 1 | 1 |  |  |  | 1 |
| Dry Flo ® Plus |  |  |  |  |  |  |  |  |  |  |  |
| SFE 839 |  |  |  |  |  |  |  | 3 |  |  |  |
| Emery ® 1780 | 1 |  |  |  |  |  |  |  |  |  | 1 |
| Lanolin; anhydrous USP |  |  | 5 |  |  |  |  |  |  | 4 |  |
| Cyclohexyl cyclohexane | 3 | 4 | 2 | 12 | 10 | 2 | 2 | 6 | 3 | 12 | 1 |
| Cegesoft ® C 17 |  |  | 3 |  |  |  |  |  |  | 1 |  |
| Myritol ® PC |  |  |  |  |  | 2 |  | 4 |  |  |  |
| Myritol ® 331 | 6 |  |  |  | 2 | 6 | 2 |  |  |  | 8 |
| Finsolv ® TN |  |  |  | 5 |  | 2 | 5 |  |  |  |  |
| Cetiol ® A |  | 6 |  |  | 4 |  |  |  |  |  |  |
| Cetiol ® CC |  | 8 |  |  | 2 | 2 | 2 |  |  |  | 5 |
| Cetiol ® SN |  | 5 |  |  |  |  |  | 3 |  |  |  |
| Cetiol ® OE | 3 |  |  |  | 4 |  | 2 |  | 4 | 2 |  |
| Dow Corning DC ® 244 |  |  |  |  | 1 |  | 2 |  |  |  |  |
| Dow Corning DC ® 2502 |  |  | 1 |  | 2 |  |  |  |  |  |  |
| Prisorine ® 3758 |  |  |  |  | 3 |  |  |  |  |  |  |
| Silikonöl Wacker AK ® 350 |  |  |  | 4 |  |  |  | 3 |  |  |  |
| Cetiol ® 868 |  |  |  |  |  |  |  |  |  | 2 | 7 |
| Cetiol ® J 600 |  |  | 4 |  |  | 2 |  |  |  |  |  |
| Ceraphyl ® 45 |  |  |  | 2 |  |  |  | 2 |  | 6 |  |
| Mineral oil |  |  |  |  | 4 |  |  |  |  |  |  |
| Cetiol ® B |  |  | 2 | 4 |  |  |  |  |  | 3 |  |
| Eutanol ® G 16 |  | 1 |  |  |  |  |  |  |  | 3 |  |
| Eutanol ® G |  |  | 3 |  |  |  |  | 8 |  |  |  |
| Cetiol ® PGL |  |  |  |  |  | 4 |  |  | 9 |  |  |
| Almond oil |  |  |  |  | 1 |  | 5 |  |  |  |  |
| Insect Repellent ® 3535 | 2 |  |  |  |  |  |  |  |  |  |  |
| N,N-Diethyl-m-toluamide |  |  |  | 3 |  |  |  | 5 |  |  |  |
| Photonyl ® LS | 2 | 2 |  |  |  |  |  |  |  |  |  |
| Panthenol |  |  |  |  |  | 1.0 |  |  |  |  |  |
| Bisabolol |  |  |  |  |  | 0.2 |  |  |  |  |  |
| Tocopherol/Tocopheryl Acetate |  |  |  |  |  | 1.0 |  |  |  |  |  |
| Magnesium sulfate × 7 water |  |  |  |  |  | 1 |  |  |  |  |  |
| Bentone ® 38 |  |  |  |  | 1 |  |  |  |  |  |  |
| Propylene carbonate |  |  |  |  | 0.5 |  |  |  |  |  |  |
| Ethanol |  |  |  |  |  |  |  |  |  | 8 |  |
| Butylene Glycol |  |  | 2 | 6 |  |  | 2 | 5 |  |  | 2 |
| Glycerin | 5 | 3 | 3 |  | 5 | 3 | 2 |  | 10 | 4 |  |
| Water, preservative | to 100, q.s. | | | | | | | | | | |

TABLE 6

W/O care emulsions
Quantities are in % by weight of the commercially available substances in the composition as a whole

| Component | 66 | 67 | 68 | 69 | 70 | 71 | 72 | 73 | 74 | 75 | 76 |
|---|---|---|---|---|---|---|---|---|---|---|---|
| L = Lotion, C = Cream | L | C | L | L | C | L | L | L | L | C | C |
| Dehymuls ® PGPH | 3 | 1 | 5 | 1 | 1 | 3 | 3 | 4 | 1 | 1 | 1 |
| Monomuls ® 90-O18 |  |  | 1 |  | 1 |  |  |  |  |  |  |
| Lameform ® TGI |  |  |  | 4 |  |  |  |  | 1 | 3 |  |
| Abil ® EM 90 |  |  |  |  | 3 |  |  |  |  | 2 |  |
| Isolan ® PDI |  | 3 |  |  |  |  |  |  |  |  | 4 |
| Glucate ® DO | 1 |  |  |  |  |  |  |  |  |  |  |
| Arlacel ® 83 |  |  |  |  |  | 3 |  |  |  |  |  |
| Dehymuls ® FCE |  |  |  |  | 4 |  | 1 |  |  |  |  |
| Dehymuls ® HRE 7 |  |  |  |  |  |  |  |  | 7 |  |  |
| Zinc stearate |  | 2 | 2 | 1 | 1 |  | 1 | 1 |  |  | 1 |
| Microcrystalline wax |  |  |  |  | 4 |  | 1 |  |  | 4 |  |
| Beeswax |  | 4 |  | 2 |  | 2 | 1 | 1 | 2 |  | 5 |
| Tego ® Care CG |  |  |  |  |  |  |  |  |  |  |  |
| Prisorine ® 3505 | 1 | 1 |  |  |  |  | 1 | 1 |  | 1 | 1 |
| Dry Flo ® Plus | 1 |  |  |  |  |  |  |  |  |  |  |
| SFE ® 839 |  |  | 5 |  |  | 4 |  |  |  |  |  |

TABLE 6-continued

W/O care emulsions
Quantities are in % by weight of the commercially available substances in the composition as a whole

| Component | 66 | 67 | 68 | 69 | 70 | 71 | 72 | 73 | 74 | 75 | 76 |
|---|---|---|---|---|---|---|---|---|---|---|---|
| Emery ® 1780 | | | | | | | | | | | |
| Lanolin anhydrous USP | | 7 | 3 | | | | | | | | |
| Cyclohexyl cyclohexane | 3 | 4 | 4 | 8 | 10 | 2 | 8 | 6 | 3 | 12 | 7 |
| Cegesoft ® C 17 | | | 2 | | | | | | | | |
| Myritol ® PC | | | | 8 | | | | | | | |
| Myritol ® 331 | 4 | | 3 | | 5 | 3 | | | 5 | 4 | |
| Finsolv ® TN | | | 5 | | | 7 | | | | | |
| Cetiol ® A | | | | | | | | 6 | | | |
| Cetiol ® CC | 3 | | | 6 | | 3 | 3 | | | 8 | |
| Cetiol ® SN | | | | | 5 | | | | | | |
| Cetiol ® OE | | 3 | | 2 | | | 3 | | | | 8 |
| Dow Corning ® DC 244 | | 4 | | 2 | | 2 | | | | | |
| Dow Corning ® DC 2502 | | | | 1 | | | | | | | |
| Prisorine ® 3758 | | | | | | 1 | | | | | |
| Silikonöl Wacker AK ® 350 | | | 1 | | | 1 | | 4 | | | |
| Cetiol ® 868 | | | | | | | | | | | 10 |
| Cetiol ® J 600 | 4 | | 3 | | | | | | | | |
| Ceraphyl ® 45 | | | 1 | | | | | | 5 | 4 | |
| Mineral oil | | | | | | | 9 | | | | |
| Cetiol ® B | | | | | 3 | 3 | | | 2 | 2 | |
| Eutanol ® G 16 | 1 | | | | | | | | | | |
| Eutanol ® G | | | | 2 | | | | | 5 | | |
| Cetiol ® PGL | | | 10 | | | | | 6 | | | 3 |
| Almond oil | | | 2 | | 5 | | 2 | | | | |
| Photonyl ® LS | | | | 2 | | | | | | | 2 |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate × 7 water | | | | | | 1 | | | | | |
| Bentone ® 38 | | | | | | 1 | | | | | |
| Propylene carbonate | | | | | | 0.5 | | | | | |
| Ethanol | | | | 8 | 10 | | | | | | |
| Butylene glycol | 5 | 1 | | 3 | 3 | | | | 8 | 2 | 1 |
| Glycerin | | | 6 | 2 | | | | 5 | 5 | 3 | 5 |
| Water, preservative | | | | | | to 100, q.s. | | | | | |

TABLE 7

O/W care emulsions
Quantities are in % by weight of the commercially available substances in the composition as a whole

| Component | 77 | 78 | 79 | 80 | 81 | 82 | 83 | 84 | 85 | 86 | 87 |
|---|---|---|---|---|---|---|---|---|---|---|---|
| L = Lotion, C = Cream | C | C | C | L | C | L | L | C | L | C | C |
| Eumulgin ® VL 75 | | | | | | 4 | | | | | |
| Dehymuls ® PGPH | | 2 | | | | | | | | | |
| Generol ® R | | | 1 | | | | | | | | |
| Eumulgin ® B2 | | 0.8 | | | | | | | | | |
| Tween ® 60 | | | | 1 | | | | | | | |
| Cutina ® E 24 | | | 0.6 | 2 | | | | | | | |
| Hostaphat ® KL 340 N | | | | | | | | | 2 | | |
| Lanette ® E | | | | | | | | 1 | | | |
| Amphisol ® K | | 0.5 | | | | 1 | | | | 1 | 0.5 |
| Sodium stearate | | | | | 0.5 | | | | | | |
| Emulgade ® PL 68/50 | | 2.5 | | | | | | | | 4 | |
| Tego ® Care CG | | | | | | | | | | | 2 |
| Tego ® Care 450 | | | | | | | | | 5 | | |
| Cutina ® MD | | 1 | | 6 | 5 | | 4 | | | 6 | |
| Lanette ® 14 | | | | 1 | | | | 2 | | | 4 |
| Lanette ® O | 4.5 | | 4 | | 1 | 2 | | | | | 2 |
| Novata ® AB | | | 1 | | | | | | | | 1 |
| Emery ® 1780 | | | | | 0.5 | 0.5 | | | | | |
| Lanolin, anhydrous, USP | | | | | | | 5 | | | | |
| Cetiol ® SB 45 | | | 1.5 | | | | 2 | | | | |
| Cyclohexyl cyclohexane | 3 | 4 | 2 | 1 | 10 | 2 | 2 | 6 | 3 | 12 | 1 |
| Cegesoft ® C 17 | | | | | | | | | | | |
| Myritol ® PC | | | | | 5 | | | | | | |
| Myritol ® 331 | 2 | 5 | 5 | | | 6 | | 12 | | | |
| Finsolv ® TN | | | 2 | | | 2 | | | 8 | | |

TABLE 7-continued

O/W care emulsions
Quantities are in % by weight of the commercially available substances in the composition as a whole

| Component | 77 | 78 | 79 | 80 | 81 | 82 | 83 | 84 | 85 | 86 | 87 |
|---|---|---|---|---|---|---|---|---|---|---|---|
| Cetiol ® CC | 4 | 6 | | | | 4 | 4 | | | | 5 |
| Cetiol ® OE | | | | | | | | | 4 | 3 | |
| Dow Coming DC ® 245 | | | 2 | | 5 | 1 | | | | | |
| Dow Corning DC ® 2502 | | | | | 2 | 1 | | | | | |
| Prisorine ® 3758 | | | | | | 1 | | | | | |
| Silikonöl Wacker AK ® 350 | 0.5 | 0.5 | 0.5 | | | 1 | 4 | | | | |
| Cetiol ® 868 | | | | | 2 | | 4 | | | | |
| Cetiol ® J 600 | 2 | | 3 | | 3 | 2 | | | | 5 | |
| Ceraphyl ® 45 | | | | | | | 3 | | | | |
| Mineral oil | | | | 9 | | | | | | | |
| Cetiol ® SN | | | 5 | | | | | | | | |
| Cetiol ® B | | | | | | | | | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | 1 | | | | | |
| Bisabolol | | | | | | 0.2 | | | | | |
| Tocopherol/Tocopherylacetate | | | | | | 1 | | | | | |
| Veegum ® ultra | | | | | | | | | 1 | | |
| Keltrol ® T | | | 0.4 | | | | | | 0.5 | | |
| Pemulen ® TR 2 | 0.3 | | | | | | | 0.3 | | | |
| Carbopol ® Ultrez 10 | | 0.3 | 0.3 | 0.2 | 0.2 | 0.2 | | | 0.1 | 0.3 | 0.2 |
| Ethanol | | | | | | | | | | 10 | |
| Butylene glycol | | | | 4 | 3 | | | 2 | 5 | 2 | |
| Glycerin | 2 | 5 | 5 | | 3 | 3 | 2 | | 4 | | 3 |
| Water, preservative, NaOH | | | | | | to 100, q.s., pH 6.5-7.5 | | | | | |

TABLE 8

O/W care emulsions
Quantities are in % by weight of the commercially available substances in the composition as a whole

| Component | 88 | 89 | 90 | 91 | 92 | 93 | 94 | 95 | 96 | 97 | 98 |
|---|---|---|---|---|---|---|---|---|---|---|---|
| L = Lotion, C = Cream | C | C | L | C | L | C | L | L | L | L | C |
| Eumulgin ® VL 75 | 4 | 3 | | | | | 1 | | | | 2 |
| Generol ® R | | | | | | 2 | | | | | |
| Eumulgin ® B2 | | | | | | 2 | | | | 1 | |
| Tween ® 60 | | | | | | | | | | 1 | |
| Cutina ® E 24 | | | | 2 | | | | | | | |
| Hostaphat ® KL 340 N | | | | | | | | | | | |
| Lanette ® E | 0.5 | | | | | | | | | | 1 |
| Amphisol ® K | 0.5 | 1 | | | | | | 1 | 1 | | |
| Sodium stearate | | | | | 1 | | | | | | |
| Emulgade ® PL 68/50 | | | 6 | | | | | 5 | | | 4 |
| Tego ® Care CG | | | | | | | | | | | |
| Tego ® Care 450 | | | | | | | | | 4 | | |
| Cutina ® MD | 3 | | 3 | 8 | 6 | 8 | | | | 4 | |
| Lanette ® 14 | | 2 | | | | | | 2 | | 1 | |
| Lanette ® O | 2 | | | 2 | | 3 | 1 | | 1 | 1 | 6 |
| Novata ® AB | | | | | | | | | | | |
| Emery ® 1780 | | | | | | | | | | | |
| Lanolin, anhydrous, USP | | | | | | 4 | | | | | |
| Cetiol ® SB 45 | | | | | | | 2 | | | | |
| Cyclohexyl cyclohexane | 3 | 4 | 2 | 1 | 10 | 2 | 2 | 6 | 3 | 12 | 1 |
| Cegesoft ® C 17 | 4 | | | | | | | | | | |
| Myritol ® PC | 6 | | | | | 5 | | | 5 | | |
| Myritol ® 331 | 5 | | 5 | | | | 7 | | | 10 | 3 |
| Finsolv ® TN | | 5 | | | 5 | | | 3 | 3 | | 1 |
| Cetiol ® CC | | | | | | | | | | | 2 |

TABLE 8-continued

O/W care emulsions
Quantities are in % by weight of the commercially available substances in the composition as a whole

|  | 88 | 89 | 90 | 91 | 92 | 93 | 94 | 95 | 96 | 97 | 98 |
|---|---|---|---|---|---|---|---|---|---|---|---|
| Cetiol ® OE |  |  |  |  | 2 | 2 |  | 5 |  |  |  |
| Dow Corning DC ® 245 |  | 2 |  | 1 |  |  |  |  | 8 |  | 2 |
| Dow Corning DC ® 2502 |  | 1 |  | 1 |  |  |  |  |  |  | 3 |
| Prisorine ® 3758 | 3 |  |  |  |  |  |  |  |  |  | 2 |
| Silikonöl Wacker AK ® 350 |  |  |  | 1 |  |  |  |  |  |  | 1 |
| Cetiol ® 868 |  | 2 |  |  |  |  |  |  |  |  |  |
| Cetiol ® J 600 |  | 2 |  |  |  |  |  |  |  |  |  |
| Ceraphyl ® 45 |  |  |  |  |  |  | 3 |  |  |  |  |
| Komponente |  |  |  |  |  |  |  |  |  |  |  |
| Cetiol ® SN |  |  |  |  |  |  |  |  |  |  |  |
| Cetiol ® B |  |  | 5 |  |  | 5 |  | 4 |  |  | 3 |
| Eutanol ® G |  | 3 | 5 |  | 5 |  |  |  |  |  |  |
| Cetiol ® PGL |  |  |  |  |  |  |  | 5 | 2 |  |  |
| Dry Flo ® Plus |  | 1 |  |  |  |  |  |  |  |  | 1 |
| SFE 839 | 1 | 1 |  |  |  |  |  |  |  |  |  |
| Almond oil |  |  |  |  |  | 2 |  |  |  |  |  |
| Photonyl ® LS |  |  |  |  |  | 2 |  |  |  |  |  |
| Panthenol |  |  |  |  |  |  | 1 |  |  |  |  |
| Bisabolol |  |  |  |  |  |  | 0.2 |  |  |  |  |
| Tocopherol/ Tocopherylacetate |  |  |  |  |  |  | 1 |  |  |  |  |
| Veegum ® Ultra |  |  |  |  |  |  |  |  | 1 |  |  |
| Keltrol ® T |  |  |  |  |  |  |  |  |  | 0.5 |  |
| Carbopol ® ETD 2001 |  |  | 0.3 |  | 0.3 |  | 0.5 | 0.2 | 0.2 |  |  |
| Pemulen ® TR 2 |  |  |  | 0.3 |  |  | 0.3 |  |  |  | 0.5 |
| Ethanol |  |  | 5 |  | 8 |  |  |  |  |  | 10 |
| Butylene glycol | 5 |  |  | 2 | 3 | 3 |  |  |  | 8 |  |
| Glycerin | 2 | 4 | 3 | 3 |  |  | 7 | 5 | 3 |  | 5 |
| Water, preservative, NaOH |  |  |  |  |  |  | to 100, q.s. (pH 6.5-7.5) |  |  |  |  |

TABLE 9

Spray formulations
Quantities are in % by weight of the commercially available substances in the composition as a whole

|  | 99 | 100 | 101 | 102 | 103 | 104 | 105 | 106 | 107 | 108 | 109 |
|---|---|---|---|---|---|---|---|---|---|---|---|
| Komponente |  |  |  |  |  |  |  |  |  |  |  |
| S = Body spray, S* = Sun protection spray | S | S | S | S | S | S* | S* | S* | S* | S* | S* |
| Emulgade ® SE-PF | 8.9 |  | 7.5 | 7.5 | 4.3 | 9.8 | 8.2 | 9.9 |  |  |  |
| Eumulgin ® B2 | 3.1 |  | 3 |  |  |  |  | 4.2 |  |  |  |
| Eumulgin ® B3 |  |  |  |  | 4.2 | 4.2 | 3.3 |  |  |  |  |
| Eumulgin ® HRE 40 |  |  |  |  | 4.7 |  |  |  |  |  |  |
| Cutina ® E 24 |  | 5.9 |  | 4 |  |  |  |  |  |  |  |
| Amphisol ® K |  |  |  |  |  |  |  |  | 1 | 1 | 1 |
| Eumulgin ® VL 75 |  |  |  |  |  |  |  |  |  |  | 2 |
| Emulgade ® PL 68/50 |  | 0.5 |  |  |  |  |  |  | 2.5 | 1 |  |
| Cutina ® MD |  | 3.1 |  |  |  |  |  |  |  |  |  |
| Antaron V 220 |  |  |  |  |  | 1 | 1 | 1 |  | 1 | 1 |
| Cyclohexyl cyclohexane | 11 | 5 | 7 | 7 | 7 | 5 | 4 | 5 | 5 | 4 | 6 |
| Myritol ® PC |  |  |  |  |  |  |  |  |  |  |  |
| Myritol ® 331 |  |  | 3 | 4 | 3 | 3 | 3 | 3 |  |  |  |
| Finsolv ® TN |  | 4 |  |  |  |  |  |  | 8 |  |  |
| Cetiol ® CC | 6 |  |  | 5 | 5 | 2 | 2 | 4 |  |  |  |
| Cetiol ® OE |  | 5 | 5 |  |  | 2 |  |  |  |  |  |
| Dow Corning DC ® 244 |  | 4 | 4 | 5 |  |  |  |  |  |  |  |
| Cetiol ® 868 | 3 |  |  |  |  |  |  |  |  |  |  |
| Cetiol ® J 600 |  |  |  | 2 | 2 |  |  |  |  |  |  |
| Mineral oil |  |  | 2 |  |  |  |  |  |  |  |  |
| Cetiol ® B |  |  |  |  |  |  | 2 |  |  |  |  |
| Eutanol ® G | 2 |  |  |  | 1 |  |  |  |  |  |  |
| Photonyl ® LS | 2 |  |  |  |  |  | 2 |  |  | 2 | 2 |
| Panthenol |  |  |  |  |  | 1 |  |  |  |  |  |
| Bisabolol |  |  |  |  |  |  | 0.2 |  |  |  |  |
| Tocopherol/ |  |  |  |  |  | 1 |  |  |  |  |  |

TABLE 9-continued

Spray formulations
Quantities are in % by weight of the commercially available substances in the composition as a whole

| | 99 | 100 | 101 | 102 | 103 | 104 | 105 | 106 | 107 | 108 | 109 |
|---|---|---|---|---|---|---|---|---|---|---|---|
| Tocopherylacetate | | | | | | | | | | | |
| Neo Heliopan ® Hydro (Na salt) | | | | | | 2 | | | | 3 | |
| Neo Heliopan AP (Na salt) | | | | | | 2 | 2 | 2 | | | 1 |
| Eusolex ® OCR | | | | | | | 2 | | | | 3 |
| Neo Heliopan ® BB | | | | | | | | | | 1 | |
| Neo Heliopan ® MBC | | | | | | 2 | 2 | 2 | | 1 | 1 |
| Neo Heliopan ® OS | | | | | | 5 | | | | | |
| Neo Heliopan ® AV | | | | | | 6 | 6 | 2 | | 7.5 | 2 |
| Uvinul ® T 150 | | | | | | 1 | 1 | 1 | | 1 | |
| Parsol ® 1789 | | | | | | 1 | | 1 | | 1 | |
| Z-Cote ® HP 1 | | | | | | | | | | 2 | 2 |
| Eusolex ® T 2000 | | | | | | | | | | 2 | 2 |
| Component | | | | | | | | | | | |
| Veegum ® Ultra | | | | | | | | | | 1.5 | |
| Laponite ® XLG | | | | | | | | | 1.5 | | |
| Keltrol ® T | | | | | | | | | | | 0.5 |
| Pemulen ® TR 2 | | | | | | | | | 0.2 | | |
| Insect Repellent ® 3535 | 1 | | | | | | | | | | |
| N,N-Diethyl-m-toluamide | | 1 | | | | | | | | | |
| Ethanol | | | | | | | | | | | |
| Butylene glycol | | | | | | | 1 | | | 2 | 1 |
| Glycerin | | | | | | 3 | 2 | 3 | 2 | | 3 |
| Water/preservative/NaOH | | | | | | to100/q.s./q.s | | | | | |

APPENDIX

1) Abil® EM 90
INCI: Cetyl Dimethicone Copolyol
Manufacturer: Tego Cosmetics (Goldschmidt)
2) Amphisol® K
INCI: Potassium Cetyl Phosphate
Manufacturer: Hoffmann La Roche
3) Antaron® V 220
INCI: PVP/Eicosene Copolymer
Manufacturer: GAF General Aniline Firm Corp. (IPS-Global)
4) Antaron® V 216
INCI: PVP/Hexadecene Copolymer
Manufacturer: GAF General Aniline Firm Corp. (IPS-Global)
5) Arlacel® 83
INCI: Sorbitan Sesquioleate
Manufacturer: Uniqema (ICI Surfacants)
6) Arlacel® P 135
INCI: PEG-30 Dipolyhydroxystearate
Manufacturer: Uniqema (ICI Surfacants)
7) Bentone® 38
INCI: Quaternium-18 Hectorite
Manufacturer: Rheox (Elementis Specialties)
8) Carbopol® 980
INCI: Carbomer
Manufacturer: Goodrich
9) Carbopol® 2984
INCI: Carbomer
Manufacturer: Goodrich
10) Carbopol® ETD 2001
INCI: Carbomer
Manufacturer: BF Goodrich
11) Carbopol® Ultrez 10
INCI: Carbomer
Manufacturer: Goodrich
12) Cegesoft® C 17
INCI: Myristyl Lactate
Manufacturer: Cognis Deutschland GmbH, Grünau
13) Ceraphyl®45
INCI: Diethylhexyl Malate
Manufacturer: International Specialty Products
14) Cetiol® 868
INCI: Ethylhexyl Stearate
Manufacturer: Cognis Deutschland GmbH
15) Cetiol® A
INCI: Hexyl Laurate
Manufacturer: Cognis Deutschland GmbH
16) Cetiol® B
INCI: Butyl Adipate
Manufacturer: Cognis Deutschland GmbH (Henkel)
17) Cetiol® J 600
INCI: Oleyl Erucate
Manufacturer: Cognis Deutschland GmbH
18) Cetiol® OE
INCI: Dicaprylyl Ether
Manufacturer: Cognis Deutschland GmbH
19) Cetiol® PGL
INCI: Hexyldecanol, Hexyldecyl Laurate
Manufacturer: Cognis Deutschland GmbH
20) Cetiol® CC
INCI: Dicaprylyl Carbonate
Manufacturer: Cognis Deutschland GmbH
21) Cetiol® SB 45
INCI: Shea Butter Butyrospermum Parkii (Linne)
Manufacturer: Cognis Deutschland GmbH
22) Cetiol® SN
INCI: Cetearyl Isononanoate
Manufacturer: Cognis Deutschland GmbH (Henkel)
23) Cutina® E 24
INCI: PEG-20 Glyceryl Stearate
Manufacturer: Cognis Deutschland GmbH 24) Cutina® MD
INCI: Glyceryl Stearate
Manufacturer: Cognis Deutschland GmbH
25) Dehymuls® FCE
INCI: Dicocoyl Pentaerythrityl Distearyl Citrate
Manufacturer: Cognis Deutschland GmbH
26) Dehymuls® HRE 7
INCI: PEG-7 Hydrogenated Castor Oil
Manufacturer: Cognis Deutschland GmbH
27) Dehymuls®PGPH
INCI: Polyglyceryl-2 Dipolyhydroxystearate
Manufacturer: Cognis Deutschland GmbH
28) Dow Corning® 244 Fluid
INCI: Cyclomethicone
Manufacturer: Dow Corning
29) Dow Corning® 245 Fluid
INCI: Cyclopentasiloxane Cyclomethicone
Manufacturer: Dow Corning
30) Dow Corning® 2502
INCI: Cetyl Dimethicone
Manufacturer: Dow Corning
31) Dry®Flo Plus
INCI: Aluminium Starch Octenylsuccinate
Manufacturer: National Starch
32) Elfacos®ST 37
INCI: PEG-22 Dodecyl Glycol Copolymer
Manufacturer: Akzo-Nobel
33) Elfacos®ST 9
INCI: PEG-45 Dodecyl Glycol Copolymer
Manufacturer: Akzo-Nobel
34) Emery® 1780
INCI: Lanolin Alcohol
Manufacturer: Cognis Corporation (Emery)
35) Emulgade® PL 68/50
INCI: Cetearyl Glucoside, Ceteayl Alcohol
Manufacturer: Cognis Deutschland GmbH
36) Emulgade®SE-PF
INCI: Glyceryl Stearate, Ceteareth-20, Ceteareth-12, Cetearyl Alcohol, Cetyl Palmitate
Manufacturer: Cognis Deutschland GmbH
37) Eumulgin® B 2
INCI: Ceteareth-20
Manufacturer: Cognis Deutschland GmbH
38) Eumulgin® VL 75
INCI: Lauryl Glucoside (and) Polyglyceryl-2 Dipolyhydroxystearate (and) Glycerin
Manufacturer: Cognis Deutschland GmbH
39) Eusolex® OCR
INCI: Octocrylene
Manufacturer: Merck
40) Eusolex® T 2000
INCI: Titanium Dioxide, Alumina, Simethicone
Manufacturer: Rona (Merck)
41) Eutanol®G
INCI: Octyldodecanol
Manufacturer: Cognis Deutschland GmbH
42) Eutanol®G 16
INCI: Hexyldecanol
Manufacturer: Cognis Deutschland GmbH
43) Eutanol®G 16 S
INCI: Hexyldecyl Stearate
Manufacturer: Cognis Deutschland GmbH
44) Finsolv® TN
INCI: C 12/15 Alkyl Benzoate
Manufacturer: Findex (Nordmann/Rassmann)
45) Generol® R
INCI: Brassica Campestris (Rapseed) Sterols
Manufacturer: Cognis Deutschland GmbH
46) Glucate® DO
INCI: Methyl Glucose Dioleate
Manufacturer: NRC Nordmann/Rassmann
47) Hostaphat® KL 340 N
INCI: Trilaureth-4 Phosphate
Manufacturer: Clariant
48) Isolan® PDI
INCI: Diisostearoyl Polyglyceryl-3 Diisostearate
Manufacturer: Goldschmidt AG
49) Keltrol® T
INCI: Xanthan Gum
Manufacturer: CP Kelco
50) Lameform® TGI
INCI: Polyglyceryl-3 Diisostearate
Manufacturer: Cognis Deutschland GmbH
50) Lanette® 14
INCI: Myristyl Alcohol
Manufacturer: Cognis Deutschland GmbH
51) Lanette® E
INCI: Sodium Cetearyl Sulfate
Manufacturer: Cognis Deutschland GmbH
52) Lanette® 0
INCI: Cetearyl Alcohol
Manufacturer: Cognis Deutschland GmbH
53) Monomuls® 90-0-18
INCI: Glyceryl Oleate
Manufacturer: Cognis Deutschland GmbH
54) Myrj® 51
INCI: PEG-30-Sterate
Manufacturer: Uniqema
55) Myritol® 331
INCI: Cocoglycerides
Manufacturer: Cognis Deutschland GmbH
56) Myritol® PC
INCI: Propylene Glycol Dicaprylate/Dicaprate
Manufacturer: Cognis Deutschland GmbH
57) Neo Heliopan® 303
INCI: Octocrylene
Manufacturer: Haarmann & Reimer
58) Neo Heliopan® AP
INCI: Disodium Phenyl Dibenzimidazole Tetrasulfonate
Manufacturer: Haarmann & Reimer
59) Neo Heliopan® AV
INCI: Ethylhexyl Methoxycinnamate
Manufacturer: Haarmann & Reimer
60) Neo Heliopan® BB
INCI: Benzophenone-3
Manufacturer: Haarmann & Reimer
61) Neo Heliopan® E 1000
INCI: Isoamyl-p-Methoxycinnamate
Manufacturer: Haarmann & Reimer
62) Neo Heliopan® Hydro (Na-Salz)
INCI: Phenylbenzimidazole Sulfonic Acid
Manufacturer: Haarmann & Reimer
63) Neo Heliopan® MBC
INCI: 4-Methylbenzylidene Camphor
Manufacturer: Haarmann & Reimer
64) Neo Heliopan® OS
INCI: Ethylhexyl Salicylate
Manufacturer: Haarmann & Reimer
65) Novata® AB
INCI: Cocoglycerides
Manufacturer: Cognis Deutschland GmbH 66) Parsol® 1789
INCI: Butyl Methoxydibenzoylmethane
Manufacturer: Hoffmann-La Roche (Givaudan)
67) Pemulen® TR-2
INCI: Acrylates/C10-30 Alkylacrylate Crosspolymer
Manufacturer: Goodrich
68) Photonyl® LS
INCI: Arginine, Disodium Adenosine Triphosphate, Mannitol, Pyridoxine HCL, Phenylalanine, Tyrosine
Manufacturer: Laboratoires Serobiologiques (Cognis)
69) Prisorine® ISAC 3505
INCI: Isostearic Acid
Manufacturer: Uniqema

The invention claimed is:

1. A cosmetic composition comprising:
   (a) an aqueous phase;
   (b) an oil phase containing cyclohexyl cyclohexane wherein the cyclohexyl cyclohexane is present in the composition in an amount of from about 0.1 to 40% by weight based on the weight of the composition;
   (c) a surfactant wherein the surfactant is present in the composition in an amount of from about 1 to 30% by weight based on the weight of the composition; and
   (d) an auxiliary oil wherein the auxiliary oil component is present in the composition in an amount of from about 0.1 to 50% by weight based on the weight of the composition component.

2. The composition of claim 1 wherein the cyclohexyl cyclohexane is present in the composition in an amount of from about 0.1 to 30% by weight, based on the weight of the composition.

3. The composition of claim 1 wherein the surfactant is present in the composition in an amount of from about 5 to 25% by weight, based on the weight of the composition.

4. The composition of claim 1 wherein the surfactant is present in the composition in an amount of from about 10 to 20% by weight, based on the weight of the composition.

5. The composition of claim 1 wherein the auxiliary oil component is present in the composition in an amount of from about 5 to 25% by weight, based on the weight of the composition.

6. The composition of claim 1 wherein the auxiliary oil component is present in the composition in an amount of from about 5 to 15% by weight, based on the weight of the composition.

7. A process for treating skin or hair comprising contacting the skin or hair with a composition containing:
   (a) an aqueous phase;
   (b) an oil phase containing cyclohexyl cyclohexane wherein the cyclohexyl cyclohexane is present in the composition in an amount of from about 0.1 to 40% by weight based on the weight of the composition;
   (c) a surfactant wherein the surfactant is present in the composition in an amount of from about 1 to 30% by weight based on the weight of the composition; and
   (d) an auxiliary oil component wherein the auxiliary oil component is present in the composition in an amount of from about 0.1 to 50% by weight based on the weight of the composition.

8. The process of claim 7 wherein the cyclohexyl cyclohexane is present in the composition in an amount of from about 0.1 to 30% by weight, based on the weight of the composition.

9. The process of claim 7 wherein the surfactant is present in the composition in an amount of from about 5 to 25% by weight, based on the weight of the composition.

10. The process of claim 7 wherein the surfactant is present in the composition in an amount of from about 10 to 20% by weight, based on the weight of the composition.

11. The process of claim 7 wherein the auxiliary oil component is present in the composition in an amount of from about 5 to 25% by weight, based on the weight of the composition.

12. The process of claim 7 wherein the auxiliary oil component is present in the composition in an amount of from about 5 to 15% by weight, based on the weight of the composition.

* * * * *